US005948630A

United States Patent [19]
Singh et al.

[11] Patent Number: 5,948,630
[45] Date of Patent: Sep. 7, 1999

[54] METHOD AND COMPOSITION FOR REDUCING THE EFFECTS OF ENDOGENOUS ALKALINE PHOSPHATASE

[75] Inventors: Pratap Singh; Randy W. Johnson, both of Miami, Fla.

[73] Assignee: Dade Behring Inc., Deerfield, Ill.

[21] Appl. No.: 08/689,004

[22] Filed: Aug. 5, 1996

Related U.S. Application Data

[63] Continuation of application No. 08/292,166, Aug. 17, 1994, abandoned, which is a continuation of application No. 08/018,661, Feb. 17, 1993, abandoned.

[51] Int. Cl.$^6$ .......................... C12Q 1/42; G01N 33/53; C12N 9/16; A01N 43/78
[52] U.S. Cl. ........................... 435/21; 435/196; 435/7.1; 514/365; 514/368
[58] Field of Search ............................. 435/7.1, 21, 196; 514/365, 368

[56] References Cited

U.S. PATENT DOCUMENTS

| | | | |
|---|---|---|---|
| 3,325,356 | 6/1967 | Di Netta | 514/365 |
| 4,150,141 | 4/1979 | Berger | 514/368 |
| 4,220,153 | 9/1980 | Dresback | 128/260 |
| 4,517,288 | 5/1985 | Gregel et al. | 435/7 |
| 4,543,358 | 9/1985 | Quinlan | 514/368 |
| 4,781,920 | 11/1988 | Quinlan | 424/78.13 |
| 5,124,245 | 6/1992 | Cummins | 435/5 |
| 5,250,295 | 10/1993 | Shau et al. | 4245/85.2 |
| 5,478,753 | 12/1995 | Wong | 436/513 |

FOREIGN PATENT DOCUMENTS

| | | |
|---|---|---|
| 369362 | 11/1989 | European Pat. Off. . |
| 444302 | 12/1990 | European Pat. Off. . |
| 9009594 | 8/1990 | WIPO . |

OTHER PUBLICATIONS

Kobayashi et al. (1990) J. Histochem. Cytochem., 38(12), "Detection of Ouabain–Insensitive H$^+$–Transporting, K$^+$–Stimulated p–Nitrophenylphosphatase Activity in Rat Gastric Glands by Cerium–Based Cytochemistry", pp. 1895–1905.

Hsu et al. (1995) Int. J. Biochem., 27(12), "A Role for ATPase in the Mechanisms of ATP–Dependent Ca and Phosphate Deposition by Isolated Rachitic Matrix Vesicles", pp. 1349–1356.

Zinchuk et al. (1997) J. Histochem. Cytochem., 45(2), "Biochemical Properties and Cytochemical Localization of Ouabain–Insensitive, Potassium–Dependent –pNitrophenylphosphatase Activity in Rat Atrial Myocytes", pp. 177–187.

Long et al. (1979) Biochem. Med., 22(1), "Distinction Between Alkalne Phosphatase and Mg$^{2+}$–ATPase of the Human Polymorphonuclear Leukocyte", pp. 88–97.

Bhargava et al. "Tetramisole analogue . . . " J. Med. Chem. 20:4 p. 563–566 1977.

Blake et al. "A rapid, sensitive method . . . " Anal. Biochem. 136: 175–179 1984.

Ball et al. "A modified alkaline phosphatase enzyme . . . " J. Virol. Methods 37:2 p. 149–153 (1992).

Fishman, W.H., *Alkaline Phosphatase Isozymes: Recent Progress*, Clinical Biochemistry 1990; 23:99–104.

Moss, D.W., "Alkaline Phosphatase Isoenzymes," *Clinical Chemistry* 1982; 28: pp. 2007–2016.

Gorman, Eileen et al. An Overview of Automation, Principles and Practice of Immunoassay, Price, C. and Newman, D., Editors, Stockon Press., 1991, p. 234–236.

Wei J.S. et al., "Quantitative determination of high molecular weight alkaline phosphatase in patients with colorectal cancer by polyacrylamidegel electrophoresis," *Enzyme* 1990; 43:188–191.

Kihn L., et al., "High Molecular Weight Alkaline Phosphatase in Serum Has Properties Similar to the Enzyme in Plasma Membranes of the Liver," Amer. J. of Clin. Path., 1991; 96, 470–478.

Van Bell H. et al., "L–p–Bromotetramisole, a new reagent for use in measuring placental or intestinal isoenzymes of Alkaline Phosphatase in Human Serum," *Clinical Chemistry* 1977; 23:454–459.

Bowers, Jr. GN, "Buffer Conditions For Measuring ALP Activity in Human Serum," *Clinical Chemistry*, 18(Z): 97–104 (1972).

C. Kanno et al., "Selective Extraction of Marker Enzymes of Bovine Milk Fat Globule Membrane by non–ionic detergents," *Biological Abstracts*, xol. 68, No. 4, 1979, Philadelphia, PA, US, abstract No. 21757.

Narayanan S., Serum Alkaline Phosphatase Isoenzymes as Markers of Liver Disease, *Annals of Clinical and Laboratory Science* 1991; 21: pp. 12–18.

Severim G. et al, Diagnostic aspects of alkaline phosphatase: Separation of isoenzymes in normal and pathoiogical human serum by high performance liquid chromatography, *J. of Chromatography* 1991; 563:147–152.

Harmenberg U. et al., Identification and Characterization of Alkaline Phosphatase Isozymes in Human Colorectal Adenocarcinomas, *Tumor Biology* 1991:12:237–248.

*Primary Examiner*—Jon P. Weber
*Attorney, Agent, or Firm*—Cynthia G Tymeson

[57] ABSTRACT

A composition and method are disclosed to reduce the effects that endogenous alkaline phosphatase found in some human bodily fluid samples have on solid phase immunoassay systems. The composition comprises a detergent, inhibitors to alkaline phosphatase, and a buffer and may contain a substrate to alkaline phosphatase.

10 Claims, 8 Drawing Sheets

5,948,630

METHOD AND COMPOSITION FOR REDUCING THE EFFECTS OF ENDOGENOUS ALKALINE PHOSPHATASE

This application is continuation of application Ser. No. 08/292,166, file Aug. 17, 1994, now abandoned, which is a continuation of Ser. No. 08/018,661, filed Feb. 17, 1993, now abandoned.

FIELD OF THE INVENTION

The present invention relates generally to a method and composition for reducing the effects of endogenous alkaline phosphatase. In particular, this invention utilizes a composition containing a combination of detergents and inhibitors, to reduce the effects that endogenous alkaline phosphatase found in some human bodily fluid samples have on solid phase assay systems.

BACKGROUND

The Alkaline Phosphatases (ALPs) are a group of functionally similar enzymes which are found in nearly all organisms. They are magnesium and zinc containing enzymes and are inhibited by metal chelators. ALPs function to hydrolyze monophosphate esters such as phosphate esters of primary alcohols and phenols. Phosphates inhibit ALP activity. The hydrolysis reaction has an alkaline optimum pH. Whenever the term ALP or ALPs are used it can mean any one of these families of enzymes.

In organisms exhibiting tissue differentiation, ALPs appear in many of the different tissues and are named after the tissue of origin. ALPs originating from different tissues show slight differences in stability, catalytic properties and susceptibility to inhibition to a variety of inhibitors. Fishman, W. H. Alkaline Phosphatase Isozymes: Recent Progress, Clinical Biochemistry 1990; 23: pp. 99–104. For example, human ALPs from bone, liver and kidney show differential mobility on electrophoresis due to differences in their sialic acid content. Moss, D. W., Alkaline Phosphatase Isoenzymes, Clinical Chemistry 1982; 28: pp. 2007–2016.

Because of their enzymatic nature, ALPs have been used as a component in solid phase diagnostic assays as the label or indicator molecule to detect the presence or concentration of an analyte contained in a human bodily fluid sample. The label can be covalently attached to an analyte (or an analogue of the analyte) and the labeled analyte competes for a limited number of analyte receptors (e.g. antibodies) in a competitive assay format. Alternatively a label can be covalently attached to a second analyte receptor in a sandwich assay format. In both cases the label with its covalently attached analyte or analyte receptor is often called a conjugate.

The label of a conjugate must directly or indirectly produce a measurable signal. For example, the label of the conjugate can be a fluorescent or calorimetric compound or it can be an enzyme which produces a fluorescent, electrochemical, chemiluminescent, thermometric, or colorimetric signal when the enzyme reacts with a substrate molecule. The amount of signal formed is correlated with the amount of analyte in a test sample.

Enzymes are used as labels in immunoassay systems because of their amplifying effect. A single molecule of enzyme typically converts $10^3$ to $10^4$ molecules of substrate into product per minute. The product of an enzyme-substrate reaction can be measured calorimetrically, fluorometrically or by any other quantifiable methods. Ideally, enzymes should have a high catalytic activity at low substrate concentration; the enzyme should be stable at the pH required for receptor-analyte binding; the enzyme should have reactive groups through which the enzymes can be covalently linked with a minimum loss of activity; the enzyme should be stable under routine storage and assay conditions; and a test sample should not have enzyme activity.

Calf intestinal ALP is the ALP most commonly used as a label. It has a large number of free amino groups which can be used for conjugation without loss of enzyme activity. It has good stability in commonly used buffer systems at ambient temperatures and also possesses high temperature stability. Its optimum activity is seen in the pH range 9.5–10.5 but maximum signal is a complex function of buffer composition, ionic strength, pH, substrate and substrate concentrations. The buffer system for the ALP-substrate reaction is often diethanolamine or Tris and usually includes a magnesium salt such as magnesium chloride and/or zinc salts such as zinc acetate. Common substrates are para-nitrophenyl phosphate (p-NPP), 4-methylumbelliferyl phosphate (4-MUP) and 3-(2'-spiroadamantane)-4-methoxy-4-(3"-phosphoryloxy) phenyl-1,2-dioxetane (AMPPD). Some active ALP is present in normal human bodily fluids and may contribute to background signal. Generally specific binding is seen in various assay formats but is particularly evident in solid phase assays. See, Gorman, Eileen et al. An overview of automation, Principles and Practice of Immunoassay, Price, C. and Newman, D., Editors, Stockton Press; 1991: p. 234–236.

Methods have been developed to reduce non-specific binding. In solid phase assay formats one method has been to wash the reaction zone (i.e. area of the solid phase support having the receptor-analyte complex thereon) of the solid phase prior to addition of the substrate molecule with a wash solution containing detergents such as Tween or Brij. The solution may also contain salts, proteins such as Bovine Serum Albumin (BSA), or denaturants.

Another approach to reduce the effects of the human ALPs is to use inhibitors of ALPs in the substrate solution. This approach is especially useful in cases where the reaction zone of the solid phase support is not washed to remove the non-specifically bound interfering substances. For example, use of an inhibitor with unique $K_i$ properties could potentially reduce the effect of the human ALPs. $K_i$ is the concentration of the inhibitor which decreases enzyme activity by 50% (i.e. the lower the $K_i$, the more effective the inhibitor). Ideally the inhibitor should have a high $K_i$ for the ALP used in the conjugate, but a low $K_i$ for human ALPs that may be present in disease states. Common inhibitors to ALPs include L-phenylalanine, homoarginine, tetramisole and leva- misole and derivatives thereof. Recently 5,6-Dihydro-6-(2-naphthyl)imidazo-[2,1-b]thiazole has been used as an inhibitor for human ALPs. The last compound, with a $K_i$ of about 1.0 uM has been shown to be most effective as an inhibitor of ALPs in Sarcoma 180/TG ascites cells. See for example, Bhargava K. K. et al, Tetramisole analogues as inhibitors of Alkaline Phosphatase. an enzyme involved in the resistance of Neoplastic cells to 6-Thiopurines, J. Med. Chem. 1977; 20: pp. 563–566. However, even this inhibitor alone may not completely eliminate the effects of the human ALPs of different origins.

Some human bodily fluid test samples have been found to contain elevated levels of the various forms of normal molecular weight ALPs. These elevated levels are associated with a number of clinical symptoms and disease states. See for example, Narayanan S., Serum Alkaline Phosphatase Isoenzymes as Markers of Liver Disease, Annals of Clinical and Laboratory Science 1991; 21: pp. 12–18; Severim G. et al, Diagnostic aspects of alkaline phosphatase: separation of isoenzymes in normal and pathological human serum by high-performance liguid chromatography, Journal of Chromatography 1991; 563: pp. 147–152 and Harmenberg U. et al, Identification and Characterization of Alkaline Phosphatase Isozymes in Human Colorectal Adenocarcinomas, Tumor Biology 1991; 12: pp. 237–248.

Higher molecular weight forms of ALPs have been found in some human bodily fluid test samples and also have been found to be associated with many of these disease states. See for example, Wei J. S. et al, Quantitative determination of high molecular weight alkaline Phosphatase in patients with colorectal cancer by polyacrylamide gel electrophoresis, Enzyme 1990; 43: pp. 188–191 and Kihn L. et al, High-Molecular-Weight Alkaline Phosphatase in Serum Has ProDerties Similar to the Enzyme in Plasma Membranes of the Liver, Clinical Chemistry 1991; 96: pp. 470–478. The nature and origin of high molecular weight forms of ALP in disease states is not clear. Questions have been raised on whether it is a single species or whether it is ALP of normal molecular weight complexed with membrane particles or antibodies. In any event, the higher molecular weight forms are difficult to remove from the solid phase.

In diagnostic assays, human bodily fluid test samples that contain the higher molecular weight ALP or elevated levels of normal molecular weight ALP result in a related, although distinct and more serious form of non-specific binding. This problem will be referred to as serum-mediated non-specific binding. See, Gorman, Eileen et al. An overview of automation, Principles and Practice of Immunoassay, Price, C. and Newman, D., Editors, Stockton Press; 1991: p. 234. The ALP of these samples can contribute not only to the background signal of the diagnostic assay, but also can produce a falsely positive result even in the absence of the analyte of interest.

Current wash compositions utilized in solid phase diagnostic assays may have included detergents and inhibitors but are not completely effective in reducing serum-mediated binding. In particular, high molecular weight ALPs have poor washing qualities and are either not removed or only partially removed from the reaction zone of the solid support.

If the effects of the human ALP are not reduced, the human ALP of these test samples can react with the substrate molecule to produce additional signal. This will contribute to the signal generated from the ALP of the conjugate. This excess signal will lead to erroneous results in the determination of the analyte concentration. These false positive results are difficult to detect, except by comparison to a non-ALP reference assay or by factoring in the patient's medical history.

Thus, a wash solution is needed that will be stable, reliable, and effective in removing or reducing the effect of human high molecular weight ALP and elevated levels of human ALP from the reaction zone of a solid phase assay.

A continuing need exists for improved methods and compositions to correct the above deficiencies.

SUMMARY OF THE INVENTION

This invention relates to a method and composition for reducing the effects of endogenous ALP from a human bodily fluid sample in a solid phase immunoassay. The composition comprises an aqueous solution of a detergent, an inhibitor of human ALP, a buffer composition, and can include a substrate for ALP or an ALP conjugate. The detergents include, but are not limited to, NP-40 or Triton-100, or other comparable detergents or combinations thereof and can include Brij-35 as an additional detergent. The inhibitors include, but are not limited to tetramisole, levamisole, 5,6-Dihydro-6-(2-naphthyl)imidazo-[2,1-b]thiazole, other comparable inhibitors, and derivatives thereof. The buffer composition should be compatible with the ALP-substrate reaction and the other assay reagents. The substrate can be any substrate molecule which reacts with ALP to give a measurable signal. The types of measurable signals can be, but are not limited to calorimetric, fluorometric, chemiluminescent, electrochemical, or thermometric signals. The combination of the inhibitors and particular detergents in an effective buffer solution has the property of reducing or eliminating the effects of endogenous high molecular weight ALP and elevated levels of normal ALP which may be present in a human bodily fluid sample on the results of an assay.

This invention also comprises a method to reduce or eliminate the effects of endogenous normal and high molecular weight human ALPs in a solid phase assay system. The method involves contacting a bodily fluid sample with a specifically modified solid phase assay support; and washing the solid phase support with a wash solution, the wash solution comprising a detergent, an inhibitor of ALP, a substrate to ALP and a buffer which is compatible with ALP reactivity. The wash step reduces the effects of any endogenous high molecular weight ALP or elevated levels of normal molecular weight ALP in the diagnostic assay. Thus, when the signal molecule is generated by the ALP-substrate reaction the contribution to signal from any endogenous ALP will be eliminated or substantially reduced.

The advantages of the composition and method of the present invention will be better understood by reference to the following detailed description and Examples.

DETAILED DESCRIPTION OF THE INVENTION

Figure 1:
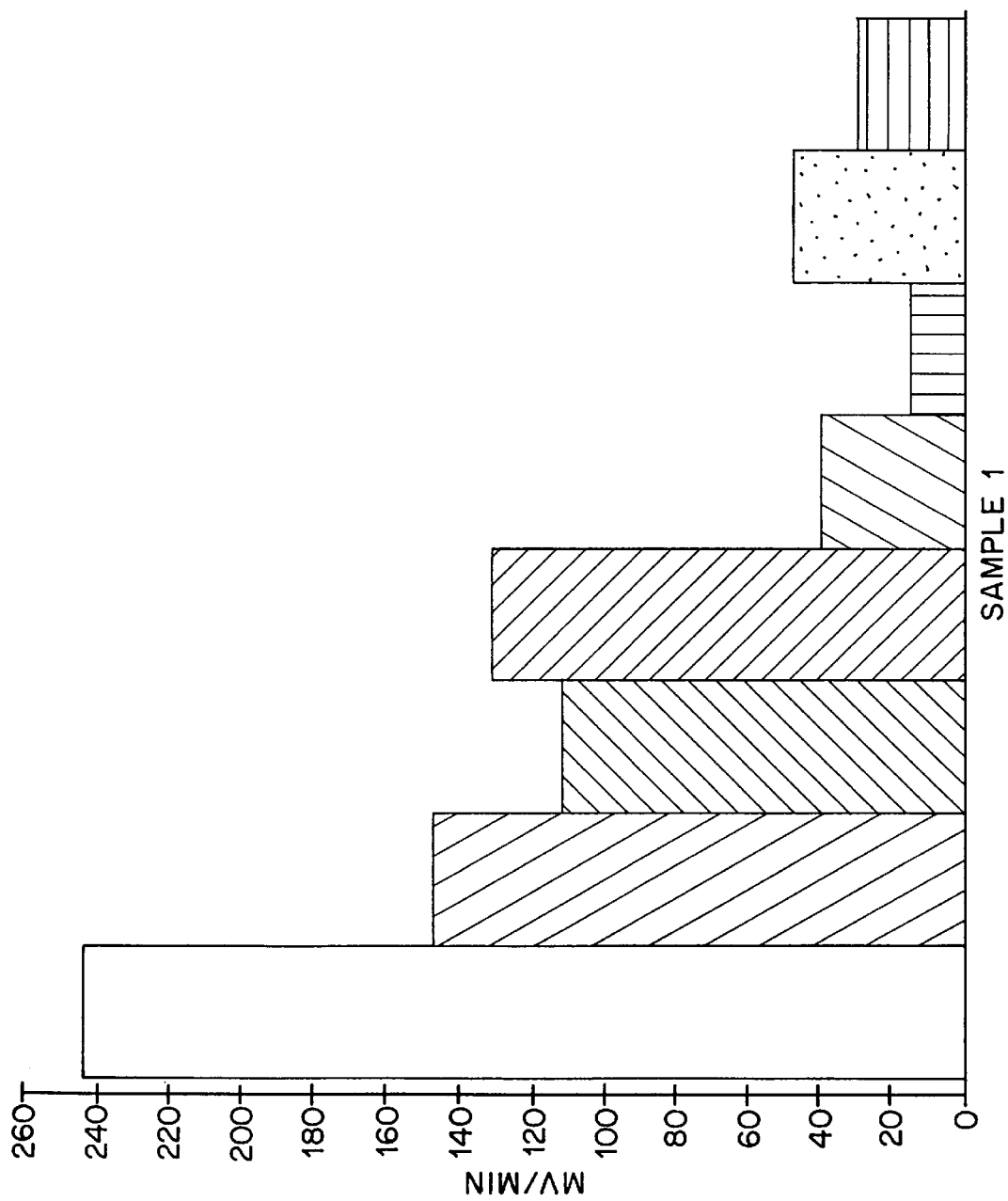
FIGS. 1–3 show comparative test results from patient serum sample (1–3 respectively) having high molecular weight alkaline phosphatase and/or elevated levels of normal alkaline phosphatase. The ability of different formulations of substrate/wash solution to decrease the background signal of alkaline phosphate was evaluated on each patient sample and compared to a commercially available formulation.

The composition of the present invention is a wash solution for use in diagnostic assays. The advantage that the present invention has over the prior art is that the wash composition of the present invention reduces the effects of high molecular weight ALP and elevated levels of normal molecular weight endogenous ALP that may be present in a human bodily fluid test sample when the sample is evaluated in a solid phase assays.

The composition of the present invention comprises an aqueous solution of a detergent, an inhibitor of human ALP, a buffer composition and can include a substrate to ALP or the ALP conjugate.

The detergents of this invention include, but are not limited to alkylphenoxy polyetheylene glycol ethers of the general formula R—$C_6H_4$—$(OCH_2CH_2)_n$OH where R is an alkyl group and n is the average number of oxyethylene monomers. In a preferred embodiment the R group is an isooctyl group containing eight carbons and the average n is between about 9 and 10. In a most preferred embodiment the detergents include, but are not limited to, the commonly known commercial products, NP-40 (Nonidet P-40) and Triton X-100 or comparable detergents and combinations thereof.

In an additional embodiment of the present invention, the composition contains a supplemental detergent. The supplemental detergents include, but are not limited to polyethylene glycol fatty alcohol ethers of the formula R—$(OCH_2CH_2)_n$OH where R is an alkyl group and n is the average number of oxyetheylene monomers. In a preferred embodiment the R group of the supplemental detergent contains more than about 10 carbons and n is more than about 20. In a most preferred embodiment the supplemental detergent is a commercially available product known as Brij-35 or a comparable detergent. The supplemental detergent is added in an amount which minimizes the effects of normal and high molecular weight human ALP in a diagnostic assay. The preferred concentration ranges of the detergent and the supplemental detergent are from about 0.5–4% detergent and most preferably from about 0.5–2% detergent. In a most preferred embodiment the detergent combinations include but are not limited to, 1–2% NP-40 and/or Triton X-100 with about 1–2% Brij-35.

The inhibitors to ALP for this invention include inhibitors which have a high $K_i$ for the ALP used in the conjugate, but a low $K_i$ for human ALPs that may be present in the human bodily fluid test samples. See for example, TABLE 1.

TABLE 1

| Inhibitor | Enzyme | $K_i$ |
| --- | --- | --- |
| Naphthyl | Conjugate | 1.4 mM |
| Naphthyl | Human Liver | 30.3 μM |
| Levamisole | Conjugate | 7.7 mM |
| Levamisole | Human Liver | 1.6 mM |
| Bromolevamisole | Human Liver | 98.5 μM |

Some inhibitors are organ specific, (see, for instance, Van Bell H. et al, L-p-Bromotetramisole, a new reagent for use in measuring placental or intestinal isoenzymes of Alkaline Phosphatase in human serum, Clinical Chemistry 1977; 23: pp. 454–459) therefore, more than one inhibitor may be added to the composition. A large variety of organic and inorganic molecules are inhibitors to ALP. They include, but are not limited to, orthophosphate, arsenate, L-phenylalanine, L-homoarginine, tetramisole, levamisole, L-p-Bromotetramisole, 5,6-Dihydro-6-(2-naphthyl)imidazo-[2,1-b]thiazole (napthyl) and derivatives thereof. The preferred inhibitors include, but are not limited to, levamisole, bromotetramisole, and 5,6-Dihydro-6-(2-naphthyl)imidazo-[2,1 b]thiazole and derivatives thereof. The most preferred inhibitors include but are not limited to, 5,6-Dihydro-6-(2-naphthyl)imidazo-[2,1-b]thiazole and derivatives thereof.

The inhibitors are added in an amount which is effective to minimize the effects of endogenous high molecular weight ALP and/or elevated levels of normal ALP that may be present in a human bodily fluid test sample in a diagnostic assay. The preferred concentration range is from about 0.2 mM to 5 mM, and the most preferred concentration range is from about 0.5 mM to 1.5 mM. Any ALP which is not washed away from the reaction zone will be inhibited.

The buffer is selected so that it is compatible with the conjugate-substrate reaction. The wash composition can include the ALP conjugate or the substrate and in some assay formats it can be particularly advantageous to include either the ALP conjugate or the substrate with the composition. For example, it is particularly advantageous to include the substrate in with the wash composition when the addition of the substrate solution could function as a wash step.

The choice of buffers is dependent on whether the ALP conjugate or the substrate are included in the wash composition. Preferably the buffer is selected to maximize the activity of the ALP conjugate-substrate reaction.

The composition of the present invention can be merely a wash solution and need not include the ALP conjugate or substrate molecule. The buffer component must be compatible with the other components that will be utilized or formed during the process of the diagnostic assay. The buffer can include but is not limited to barbital, carbonate-bicarbonate, glycine, tris(hydroxymethyl)aminoethane (TRIS), ethylaminoethanol (EAE), diethanolamine (DEA) and other transphosphorylating buffers, and amino alcohol buffers such as 2 amino-2-methyl 1-propanol (AMP). Preferred buffers include, but are not limited to transphosphorylating buffers such as DEA, TRIS, and EAE and the most preferred buffer includes but is not limited to DEA. The pH can range from about 7.0 to 10.0, preferably from about 8.0 to 9.0. The concentration of the buffer can be in the range from about 0.1 M to 2.0 M, preferably in the range from about 0.5 M to 1.5 M and most preferably about 0.8 M to 1.5 M. Salts such as sodium chloride and potassium chloride or comparable salts and proteins such as bovine serum albumin and gelatin or comparable proteins can also be included.

If the wash solution of the present invention includes the assay conjugate, the buffer component is selected so that the conjugate stability (whether it is an enzyme-antibody or enzyme-hapten) is maximized and the ALP conjugate-substrate reaction is not diminished. The buffer component can include, but is not limited to TRIS, DEA, EAE, and N-(carbamoylmethyl) taurine. The most preferred buffer is TRIS. The pH should be in a range from about 7.0 to 10.0, and most preferably from about 8.0 to 9.0. The concentration of the buffer can be in the range from about 0.1 M to 2.0 M, preferably in the range from about 0.5 M to 1.5 M and most preferably about 0.8 M to 1.5.

In a most preferred embodiment of the present invention, the wash composition includes a substrate to the ALP conjugate. The buffer conditions are selected to maximize the conjugate-substrate reaction. See Bowers, Jr. GN, Buffer Conditions for Measuring ALP Activity in Human Serum, Clinical Chemistry, 18 (2): pp. 97–104 (1972). Buffers include, but are not limited to barbital, carbonate-bicarbonate, glycine, tris(hydroxymethyl)aminoethane (TRIS), ethylaminoethanol (EAE), diethanolamine (DEA) and other transphosphorylating buffers, and amino alcohol buffers such as 2 amino-2-methyl 1-propanol (AMP). Preferred buffers include, but are not limited to transphosphorylating buffers such as DEA, TRIS, and EAE and the most preferred buffer includes but is not limited to DEA. Transphosphorylating buffers are preferred because phosphate formed in the conjugate-substrate reaction is transferred to the hydroxyl group of the transphosphorylating buffer faster than the phosphate is hydrolyzed by water. Thus the effective phosphate concentration is decreased and there is an increase in activity of the ALP conjugate. The concentration of the buffer can be in the range from about 0.1 M to 2.0 M, preferably in the range from about 0.5 M to 1.5 M and most preferably about 0.8 M to 1.5 M. The pH can be in the range from about 7.0 to 10.0 and most preferably from about 8.0 to 9.0. The buffer can include salts such as sodium chloride or potassium chloride and must include a magnesium salt such as magnesium chloride or magnesium acetate and a zinc salt, such as zinc sulfate for maximum activity.

The substrate molecule can be any substrate which will generate a measurable signal molecule such as a fluorescent, electrochemical, chemiluminescent, thermometric, or calorimetric molecule. Preferred substrates include calorimetric substrates such as p-NPP, fluorescent substrates such as 4-MUP or chemiluminescent substrates such as AMPPD. The concentration of the substrate molecule is in the range from about 1 mM to 16 mM, preferably in the range from about 1 mM to 2 mM.

The method of the present invention is a method for reducing the effects of human high molecular weight ALP and/or elevated levels of normal molecular weight ALP that may be present in a human bodily fluid test sample when the human bodily fluid test sample is evaluated to determine the presence or concentration of an analyte in a diagnostic assay, the process comprising: a) contacting the human bodily fluid test sample with a solid support to form a reaction zone on the solid support; b) contacting (under conditions promoting binding) the analyte of the human bodily fluid test sample to a receptor for the analyte; and b) washing the reaction zone of the solid support with a wash solution, the wash solution comprising a detergent, an inhibitor of human ALP, and a buffer composition. The test sample is contacted with a solid phase support and immobilized thereon. Then the solid phase is washed once or several times with the wash solution. The quantity of wash solution is sufficient to cover the reaction zone of the solid phase and to reduce the effects of the high molecular weight ALP and/or elevated levels of normal molecular weight ALP which may be present in a human bodily fluid sample in a diagnostic assay. For example if the solid phase of an assay is an ELISA plate, beads, or a tube, an amount of the wash composition sufficient to immerse the reaction zone of the solid phase is dispensed into the solid phase then aspirated from the solid phase. The wash step can be repeated.

As described above, the preferred embodiment of the wash composition comprises about 1–2% NP-40 and/or Triton X-100 or comparable detergent, 5,6-Dihydro-6-(2-naphthyl)imidazo-[2,1-b]thiazole or comparable ALP inhibitor, and a buffer that is compatible with the reagents utilized or products formed during the assay process, maximizes the conjugate ALP-substrate reaction and minimizes the endogenous ALP-substrate reaction. The wash composition may contain as a supplemental detergent about 2% Brij-35 or comparable detergent. As previously indicated, the wash composition can also include the ALP conjugate or the substrate. Thus, those compositions can perform a dual function. The first function is to reduce the effects of the endogenous ALP. The second function is to initiate the conjugate-analyte or conjugate-receptor reaction or the conjugate-substrate reaction when the wash solution is added to the solid phase support. If the wash solution includes an ALP conjugate, the solution is referred to herein as a conjugate/wash solution. If the wash solution includes a substrate, the solution is referred to herein as a substrate/wash solution. Thus, the effects of high molecular weight ALP and elevated levels of normal molecular weight ALP from a human bodily fluid sample are further reduced or alternatively a wash step of the assay procedure can be eliminated.

If the wash composition includes an ALP conjugate, the method of the present invention is a method to reduce the effects of endogenous high molecular weight ALP and/or elevated levels of normal ALP which may be present in a human bodily fluid test sample when that test sample is evaluated to determine the presence or concentration of an analyte in a diagnostic assay, the method comprising: a) contacting a human bodily fluid sample with a solid phase support to form a reaction zone on the solid phase support; b) contacting the analyte of the human bodily fluid test sample to a receptor for the analyte; c) applying a conjugate/wash solution to the reaction zone of the solid phase support, the conjugate/wash solution comprising a detergent, an inhibitor of human ALP, a buffer composition, and an ALP conjugate.

As described above, the preferred embodiment of the conjugate/wash solution comprises about 1–2% NP-40 and/or Triton X-100 or comparable detergent, 5,6-Dihydro-6-(2-naphthyl)imidazo-[2,1-b]thiazole or comparable ALP inhibitor, a buffer that maximizes the conjugate stability (whether it is an enzyme-receptor or enzyme-hapten) and does not diminish the conjugate-substrate reaction, and an ALP conjugate. The conjugate/wash composition may contain as a supplemental detergent about 2% Brij-35 or comparable detergent. The concentration of the ALP-conjugate varies considerably with the type of assay, but would be consistent with the concentration found in current conjugate compositions.

The preferred method of the present invention is a method to reduce the effects of endogenous high molecular weight ALP and elevated levels of normal molecular weight endogenous ALP which may be present in a human bodily fluid test sample when the human bodily fluid test sample is evaluated to determine the presence or concentration of an analyte in a diagnostic assay, the method comprising: a) contacting the human bodily fluid sample with a solid phase support to form a reaction zone on the solid phase support; b) contacting the analyte of the human bodily fluid test sample to a receptor for the analyte; c) applying an ALP conjugate reagent to the reaction zone; d) applying a substrate/wash solution, the substrate/wash solution comprising, a substrate to ALP, a buffer solution, a detergent, and an inhibitor of ALP.

The substrate/wash solution has the dual function of reducing the effects of any high molecular weight ALP and/or elevated levels of normal molecular weight ALP which may be present in the human test sample and initiating the ALP conjugate-substrate reaction.

As described above, the preferred embodiment of the substrate/wash solution comprises about 1–2% NP-40 and/or Triton X-100 or comparable detergent, 5,6-Dihydro-6-(2-naphthyl)imidazo-[2,1-b]thiazole or comparable ALP inhibitor, a transphosphorylating buffer such as DEA, TRIS, and EAE or comparable buffer and a substrate to ALP such as p-NPP, 4-MNUP, AMPPD or comparable ALP substrate. The substrate/wash composition may contain as a supplemental detergent about 2% Brij-35 or comparable detergent. The concentration of the substrate can vary with the type of assay, but would be consistent with the substrate concentration found in current compositions.

The solid phase is not critical and includes any of the solid phases known in the art such as plates, beads, papers and particles. However, with some solid phases it may be particularly advantageous to utilize a conjugate/wash solution, substrate/wash solution or both with or without a separate wash step. These assay systems usually utilize films, papers, or fibers (e.g. Baxter Diagnostic Inc.'s Stratus$^R$ System and Polaroid-Behring's OPUS$^R$ System) or microparticles which can be embedded into the papers or fibers (e.g. Abbott's IMX$^R$ System) as the solid phase support. The solution flows over or through the support and carries endogenous ALP out of the reaction zone. Simultaneously the conjugate-receptor or conjugate analyte reaction or the substrate-conjugate reaction occurs.

The composition and method of the present invention can be further demonstrated by the following examples.

EXAMPLE 1

Three carcinoembryonic antigen (CEA) positive patient serum samples (Samples 1, 2, and 3) were identified as having high molecular weight ALP and/or elevated levels of normal ALP. These samples were tested using the compositions of this invention. The patient samples were evaluated on an automated immunoassay analyzer (the Stratus$^R$ Fluorometric Analyzer from Baxter Diagnostics Inc.) which utilizes an ALP conjugate and a 4-MUP substrate. This automated analyzer combines the wash step with the substrate addition step. See, U.S. Pat. No. 4,517,288. The commercially available substrate composition (XWS) has the dual function of washing the solid phase and initiating the ALP reaction. The substrate composition is an aqueous solution which comprises 4-MUP, levamisole, Brij-35, and stabilizers in DEA buffer.

Seven substrate/wash composition (Compositions 1–7) of the present invention were prepared by substituting the levamisole in the XWS with about 1 mM 5,6-Dihydro-6-(2-naphthyl)imidazo-[2,1-b]thiazole (naphthyl). Additionally, the compositions differed from the commercially available substrate in that Composition 1 contained no detergents; Composition 2 contained 1.0% Brij-35; Composition 3 contained 2% Brij-35; Composition 4 contained 1% Brij-35 and 2% Triton X-100; Composition 5 contained 1% Brij-35 and 2% NP-40; Composition 6 contained 2% Brij-35 and 2% Triton X-100; and Composition 7 contained 2% Brij-35 and 2% NP-40. A summary of the compositions are presented below in TABLE 2. L represents the inhibitor levamisole and Naphthyl represents the inhibitor 5,6-Dihydro-6-(2-naphthyl)imidazo-[2,1-b]thiazole.

TABLE 2

| Composition | Inhibitor | % of Brij-35 | % of Triton X-100 | % of NP-40 |
| --- | --- | --- | --- | --- |
| XWS | L | 1 | 0 | 0 |
| 1 | Naphthyl | 0 | 0 | 0 |
| 2 | Naphthyl | 1 | 0 | 0 |
| 3 | Naphthyl | 2 | 0 | 0 |
| 4 | Naphthyl | 1 | 0 | 2 |
| 5 | Naphthyl | 1 | 2 | 0 |
| 6 | Naphthyl | 2 | 2 | 0 |
| 7 | Naphthyl | 2 | 0 | 2 |

The samples were evaluated on the analyzer using each composition as the substrate/wash. The analyzer measures the rate of change of the fluorescent signal generated from the reaction between the conjugate ALP and the substrate. The results are expressed in millivolts per minute (mv/min). Normally the signal is related to the amount of analyte present in the sample.

With these samples, the signal generated using the XWS is a result of the endogenous ALP that is neither washed because of the lack of detergents nor inhibited by the levamisole. These samples gave falsely positive results when evalutated using the XWS. With the same samples, the signal generated using Composition 1 is a result of the endogenous ALP that is not washed away because of the lack of detergents.

Figure 2:
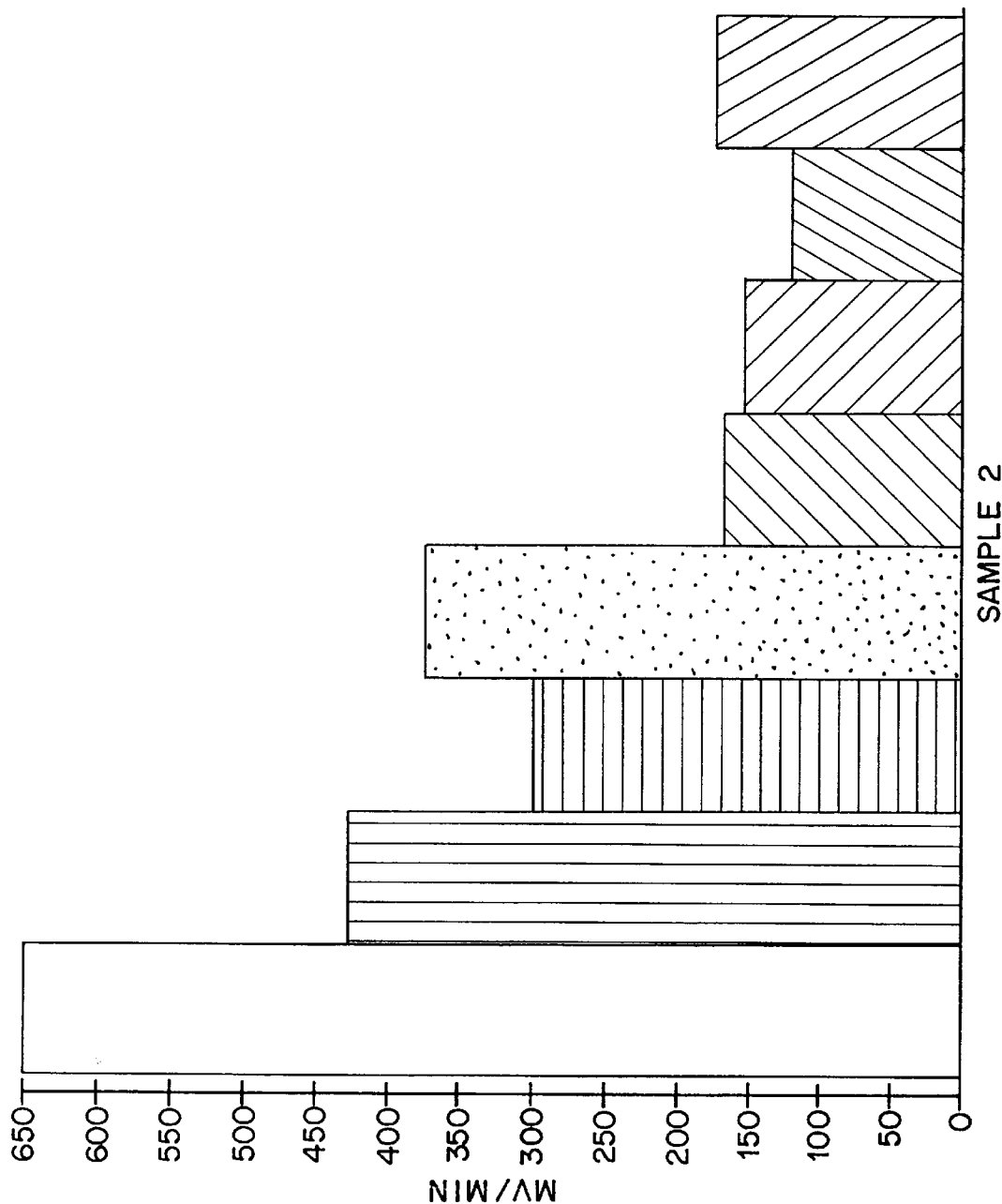
Figure 3:
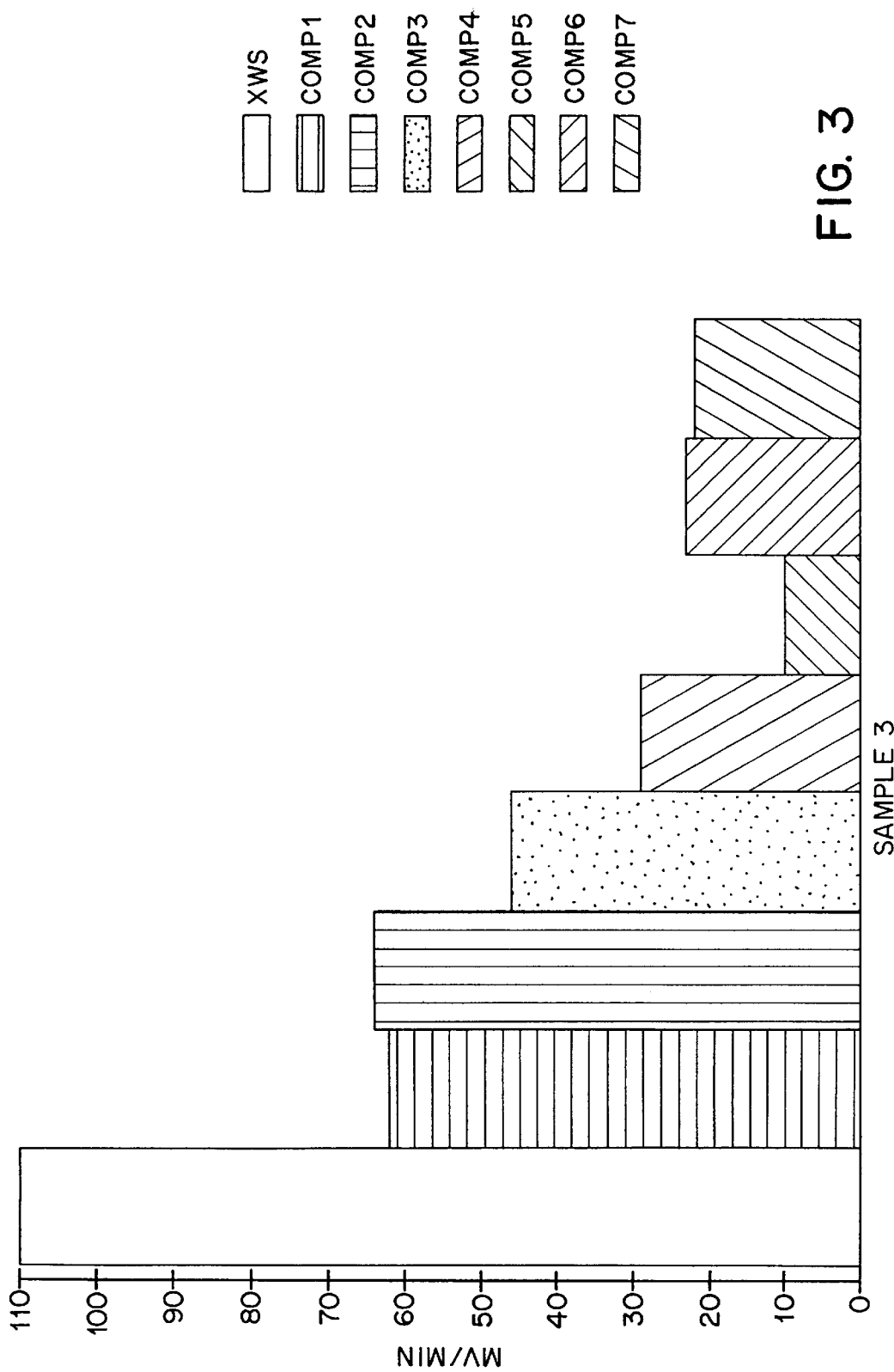
Figure 4:
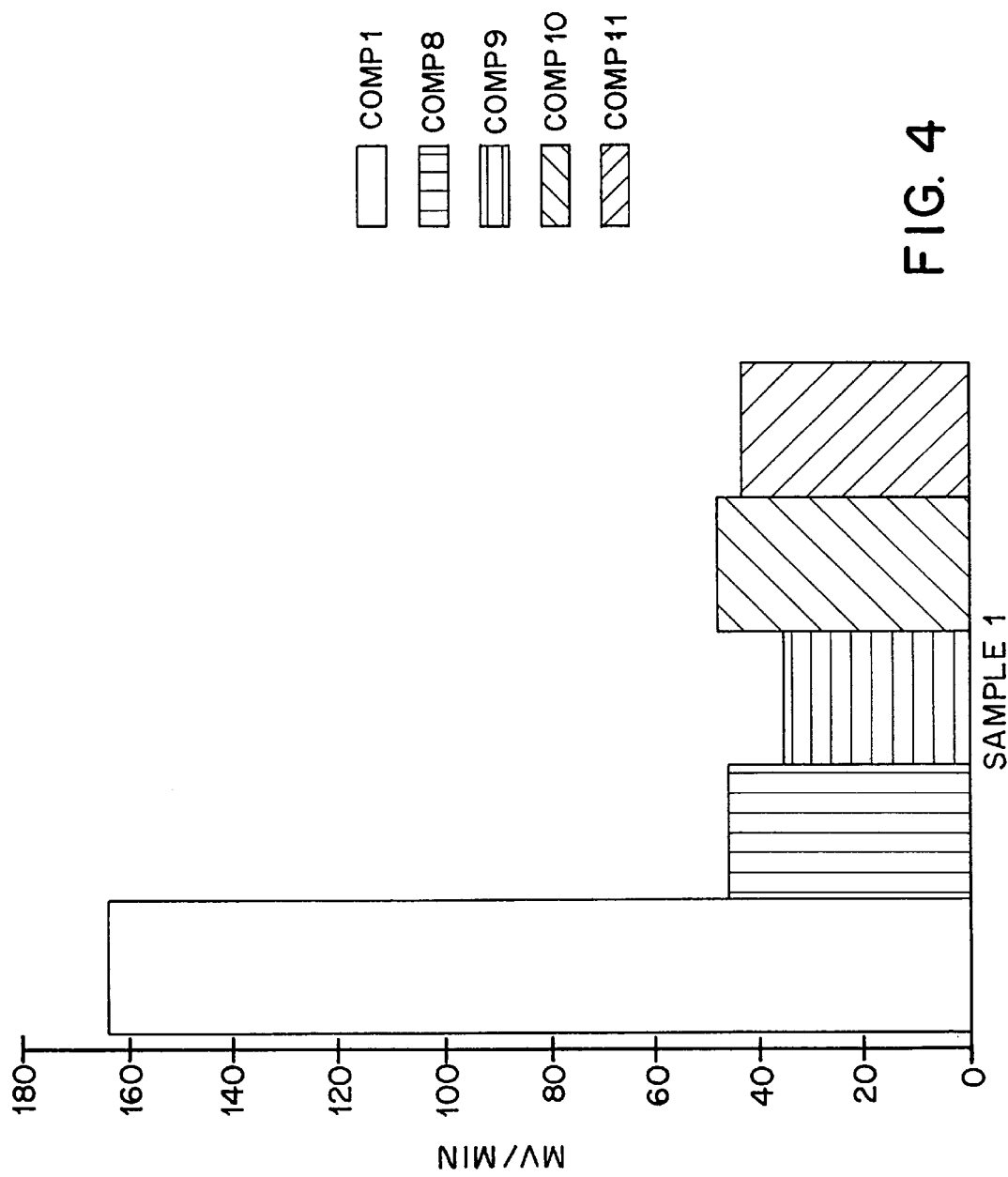
FIGS. 4–8 show comparative test results from patient serum samples (1–5 respectively) having high molecular weight alkaline phosphatase and/or elevated levels of normal alkaline phosphatase. The effect of certain detergents in a substrate/wash solution was evaluated on each patient sample.
Figure 5:
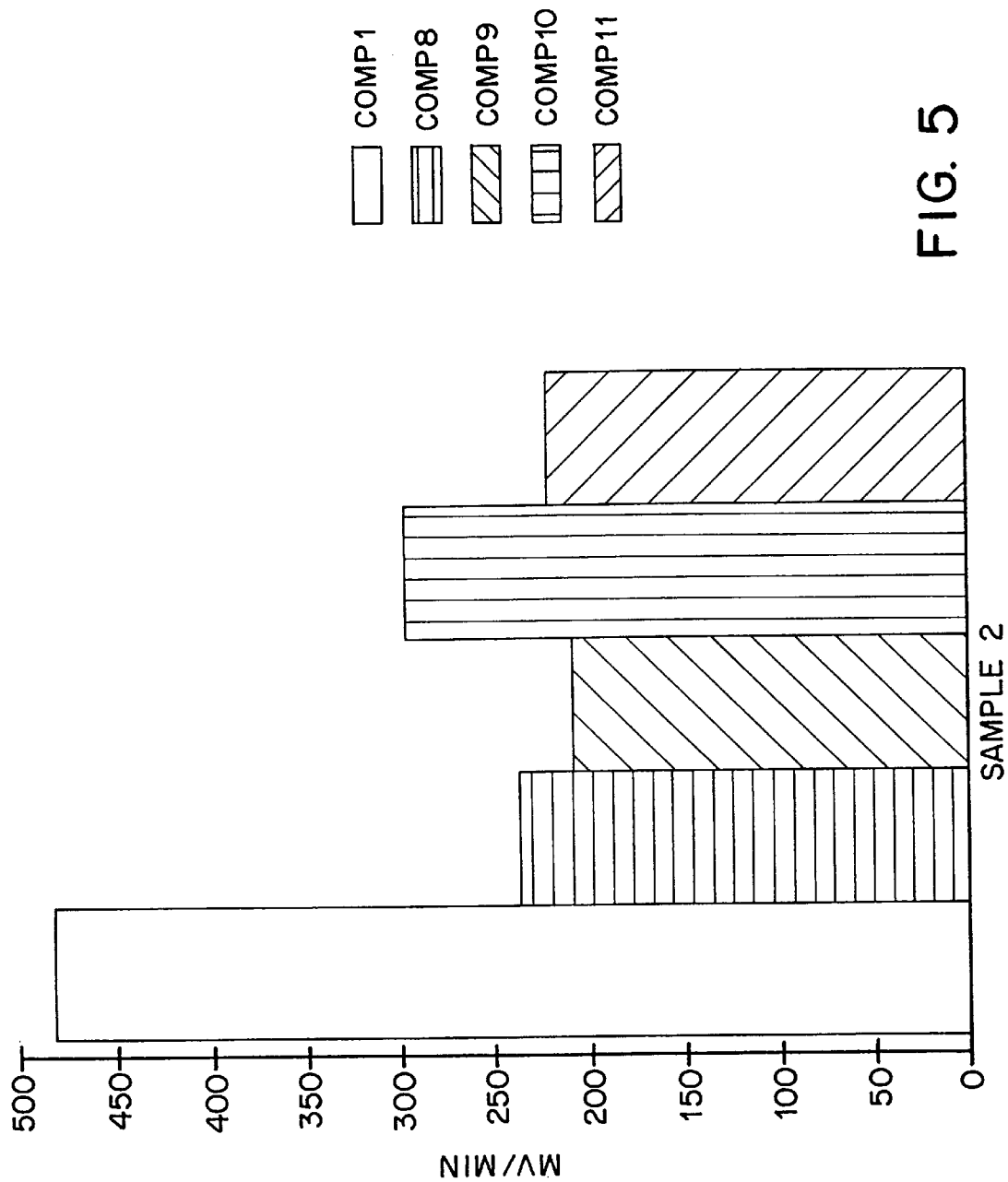
Figure 6:
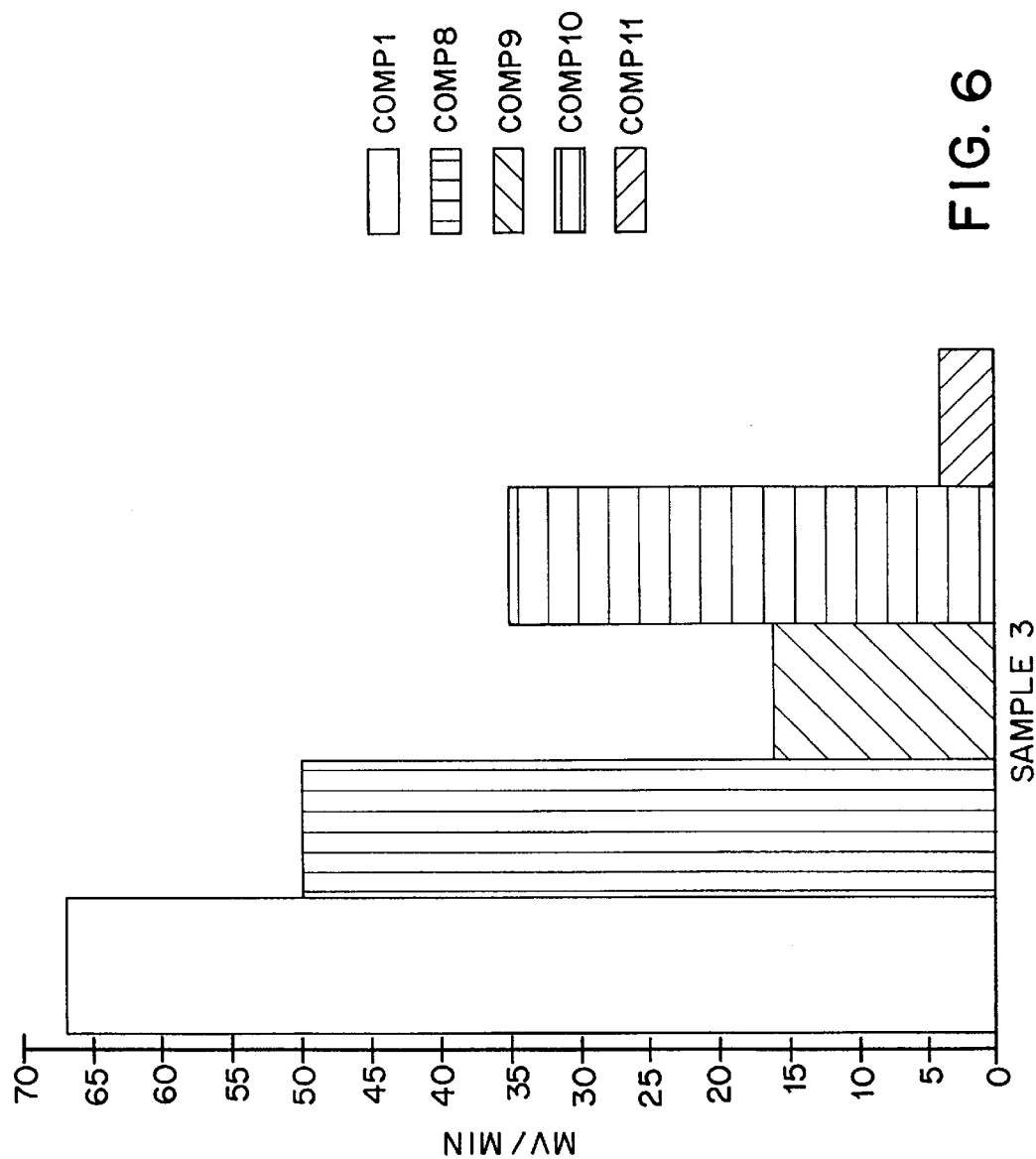
Figure 7:
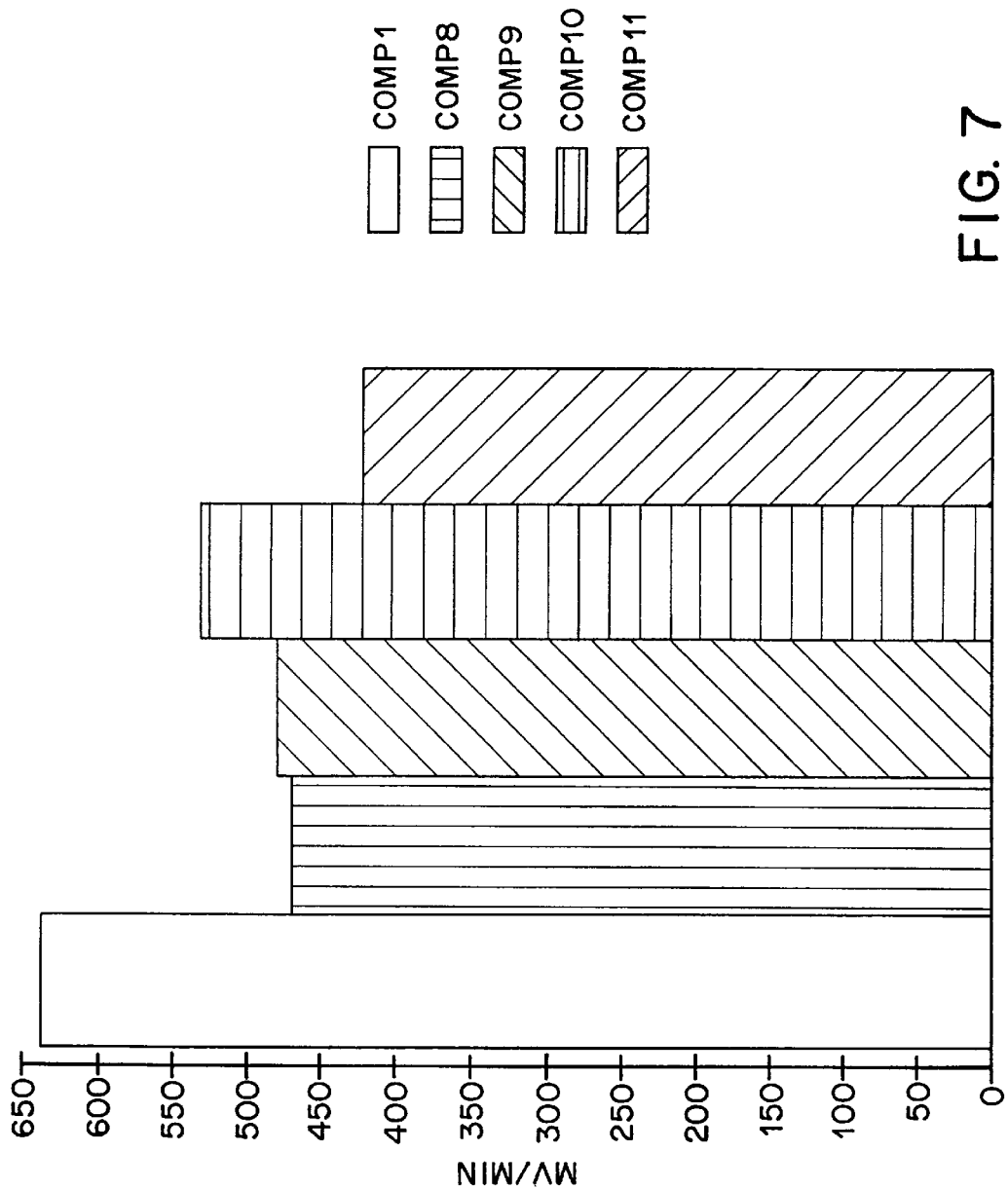
Figure 8:
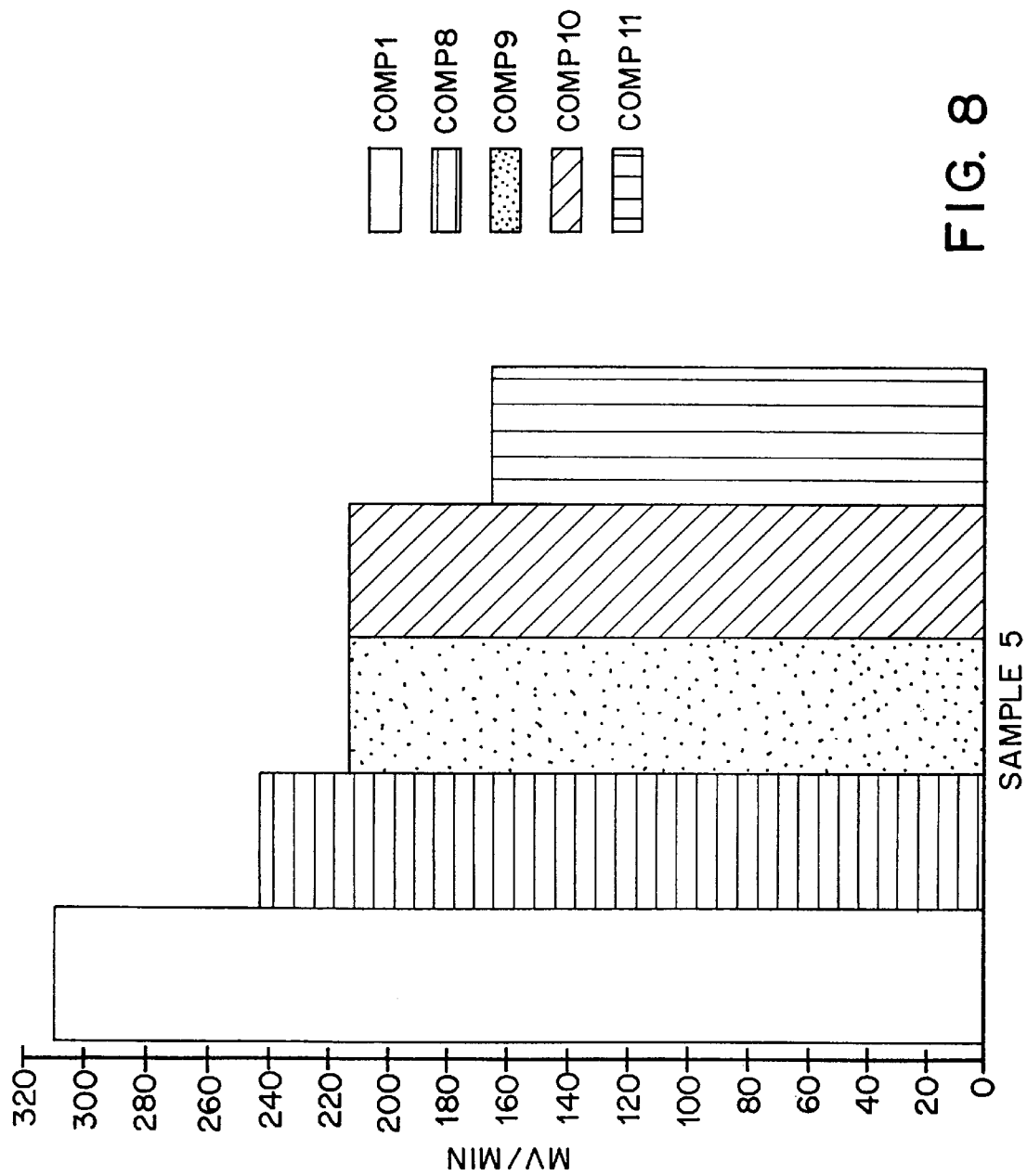

The results for Samples 1, 2, and 3 are shown in FIGS. 1, 2, and 3 respectively. As can be seen from these figures, the use of 5,6-Dihydro-6-( 2-naphthyl)imidazo-[2,1-b]thiazole as an inhibitor substantially lowers the background signal generated from the endogenous ALP in the sample, thus eliminating or substantially reducing the false positive reading. The addition of Brij-35 with compositions which also contain 5,6-Dihydro-6-(2-naphthyl)imidazo-[2,1-b] thiazolealso serves to lower the background signal. Furthermore, when additional detergents such as Triton X-100 or NP-40 are included in the composition the background signal is further decreased. Moreover, in some instances, this decrease is by more than 90% when compared with the commercially available substrate/wash composition. Therefore, the use of the 5,6-Dihydro-6-(2-naphthyl) imidazo-[2,1-b]thiazole as an inhibitor in the presence of a detergent such as Triton X-100 and/or NP-40 with or with Brij-35 is effective to eliminate or substantially reduce the effects of endogenous ALP.

EXAMPLE 2

Five patient samples, Samples 1, 2, and 3 (as described in Example 1), Sample 4 (which originated from a patient who tested positive for colon cancer) and Sample 5 (which originated from a patient who tested positive for breast cancer) were identified as having high molecular weight ALP and/or elevated levels of normal ALP. These samples were evaluated using the compositions of this invention. The patient samples were evaluated on the automated immunoassay analyzer described in Example 1.

The effects of Triton X-100 and NP-40 on these samples were investigated by preparing a substrate/wash composition of the present invention comprising about 1 aN 5,6-Dihydro-6-(2-naphthyl)imidazo-[2,1-b]thiazole, as an endogenous ALP inhibitor, about 1 mM 4-MUP, and stabilizers in about 1 M DEA (Composition 1 as in Example 1).

Four other substrate/wash composition of the present invention were prepared in the same manner as Composition 1, except Composition 8 additionally contained about 1% Triton X-100; Composition 9 additionally contained 2% Triton X-100; Composition 10 additionally contained 1% NP-40; and Composition 11 additionally contained 2% NP-40. A summary of the compositions are presented below in TABLE 3. Naphthyl represents the inhibitor 5,6-Dihydro-6-(2-naphthyl)imidazo-[2,1-b]thiazole.

TABLE 3

| Composition | Inhibitor | % of Brij-35 | % of Triton X-100 | % of NP-40 |
| --- | --- | --- | --- | --- |
| 1 | Naphthyl | 0 | 0 | 0 |
| 8 | Naphthyl | 0 | 1 | 0 |
| 9 | Naphthyl | 0 | 2 | 0 |
| 10 | Naphthyl | 0 | 0 | 1 |
| 11 | Naphthyl | 0 | 0 | 2 |

The samples were evaluated on the analyzer using each composition as the substrate/wash. The analyzer measures the rate of change of the fluorescent signal generated from the reaction between the conjugate ALP and the substrate. The results are expressed in millivolts per minute (mv/min).

The results for Samples 1 through 5 are shown in FIG. 4 to 8 respectively. When detergents such as Triton X-100 or NP-40 are included in the composition the background signal resulting from endogenous ALP is substantially decreased. Moreover, in some instances, this decrease is by more than about 90% when compared to the sample containing no detergents. These detergents were effective in eliminating or reducing the effects of endogenous ALP. Therefore, the use of the 5,6-Dihydro-6-(2-naphthyl)imidazo-[2,1-b]thiazole as an inhibitor in the presence of a detergent such as Triton X-100 and/or NP-40 with or with Brij-35 is effective to eliminate or substantially reduce the effects of endogenous ALP.

Note that Sample 4 showed the least improvement. This sample originated from a patient diagnosed as having colon cancer, thus the high molecular weight endogenous ALP may be of intestinal origin. Since the conjugate used in this study is of intestinal origin, the inhibitors are selected to not inhibit intestinal ALP.

We claim:

1. A wash composition, for use in a solid phase immunoassay having an alkaline phosphatase conjugate, wherein the wash composition reduces the effects of high molecular weight alkaline phosphatase or elevated levels of normal alkaline phosphatase which may be present in a test sample derived from blood, the wash composition comprising:
   a) at least one detergent having the formula R—$C_6H_4$-$(OCH_2CH_2)_n$OH wherein the R of the detergent is an isooctyl group containing eight carbons and n is the average number of oxyethylene monomers and the average n is between 9 and 10;
   b) at least one inhibitor to alkaline phosphatase wherein the inhibitor is selected from the group consisting of levamisole, L-p-bromotetramisole, tetramisole and 5,6-Dihydro-6-(2-naphthyl)imidazo-[2,1-b]thiazole; and
   c) a buffer.

2. The wash composition of claim 1 wherein the composition further comprises a second detergent, said second detergent having the formula R—$(OCH_2CH_2)_n$OH wherein R is an alkyl group and n is the average number of oxyethylene monomers.

3. The wash composition of claim 2 wherein the R group of the second detergent contains at least 10 carbons and the n of the second detergent is at least 10.

4. The wash composition of claim 1 further comprising a substrate to alkaline phosphatase.

5. The wash composition of claim 1 wherein the buffer is selected from the group consisting of diethanolamine, ethylaminoethanol, and tris (hydroxymethyl)aminoethane.

6. A method for use in a solid phase immunoassay which utilizes an alkaline phosphatase conjugate, to substantially reduce the effects of high molecular weight alkaline phosphatase and elevated level of nomal alkaline phosphatase which may be present in a patient sample, the method comprising:

a) contacting the sample with a solid support to form a reaction zone on the solid support;
   b) contacting the analyte of the sample to a receptor for the analyte; and
   c) washing the reaction zone of the solid support with a wash composition comprising i) at least one detergent having the formula R—$C_6H_4$—$(OCH_2CH_2)_n$OH wherein the R of the detergent is an isooctyl group containing eight carbons and n is the average number of oxyethylene monomers and the average n is between 9 and 10;
      ii) at least one inhibitor to alkaline phosphatase wherein the inhibitor is selected from the group consisting of levamisole, L-p-bromotetramisole, tetramisole and 5,6-Dihydro-6-(2-naphthyl)imidazo-[2,1-b]thiazole; and
      iii) a buffer.

7. The method of claim 6 wherein the wash composition further comprises a second detergent, said second detergent having the formula R—$(OCH_2CH_2)_n$OH wherein R is an alkyl group and n is the average number of oxyethylene monomers.

8. The method of claim 6 wherein the wash composition further comprises a substrate to alkaline phosphtase.

9. The method of claim 6 wherein the buffer of the wash composition is selected from the group consisting of diethanolamine, ethylaminoethanol, and tris (hydroxmethyl) aminoethane.

10. A wash composition, for use in a solid phase immunoassay having an alkaline phosphatase conjugate, wherein the wash composition reduces the effects of high molecular weight alkaline phosphatase or elevated levels of normal alkaline phosphatase which may be present in a test sample derived from blood, the wash composition comprising:
   a) at least one detergent having the formula R—$C_6H_4$—$(OCH_2CH_2)_n$OH wherein the R of the detergent is an isooctyl group containing eight carbons and n is the average number of oxyethylene monomers and the average n is between 9 and 10;
   b) at least one inhibitor to alkaline phosphatase wherein the inhibitor is selected from the group consisting of levamisole, L-p-bromotetramisole, tetramisole and 5,6-Dihydro-6-(2-naphthyl)imidazo-[2,1-b]thiazole or derivatives thereof wherein such derivative has a $K_i$ to high molecular weight alkaline phosphatase or elevated levels of normal alkaline phosphatase less than or equal to the $K_i$ of the inhibitor from which it was derived; and
   c) a buffer.

* * * * *